(12) United States Patent
Siggel et al.

(10) Patent No.: US 9,064,633 B2
(45) Date of Patent: *Jun. 23, 2015

(54) METHOD FOR SYNTHESIZING QUATERNARY AMMONIUM SYSTEMS

(71) Applicant: Honeywell International Inc., Morristown, NJ (US)

(72) Inventors: Alfred Siggel, Seelze (DE); Frank Nerenz, Seelze (DE); Thirumalai Palanisamy, Morristown, NJ (US); Andrew Poss, Kenmore, NY (US); Sonja Demel, Wunstorf (DE)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/846,805

(22) Filed: Mar. 18, 2013

(65) Prior Publication Data
US 2013/0264510 A1    Oct. 10, 2013

Related U.S. Application Data

(62) Division of application No. 11/511,938, filed on Aug. 28, 2006, now Pat. No. 8,426,593.

(51) Int. Cl.
*H01G 9/035* (2006.01)
*C07D 471/10* (2006.01)
*C07D 487/10* (2006.01)

(52) U.S. Cl.
CPC .............. *H01G 9/035* (2013.01); *C07D 471/10* (2013.01); *C07D 487/10* (2013.01)

(58) Field of Classification Search
CPC ...................................................... C07D 487/10
USPC ........................................... 546/16; 548/408
See application file for complete search history.

(56) References Cited

U.S. PATENT DOCUMENTS

| | | | |
|---|---|---|---|
| 4,351,939 A | 9/1982 | Simms et al. | |
| 5,086,178 A | 2/1992 | Banks | |
| 6,469,888 B1 | 10/2002 | Otsuki et al. | |
| 8,426,593 B2 * | 4/2013 | Siggel et al. | 546/15 |

FOREIGN PATENT DOCUMENTS

| | | |
|---|---|---|
| EP | 0478210 A1 | 4/1992 |
| EP | 1659598 A1 | 5/2006 |
| WO | WO 2004/099152 A1 | 11/2004 |
| WO | WO 2005/022571 A1 | 3/2005 |

OTHER PUBLICATIONS

Ooi, T. et al., "Design of N-Spiro C2-Asymmetric Chiral of Quaternary Ammonium Bromides as Novel Chiral Phase-Transfer Catalysts: Synthesis and Application to Practical Asymmetric Synthesis of of Alpha-Amino Acids", Journal of the American Chemical Society, 2003, vol. 125, pp. 5139-5151.
Arai, S. et al., "Phase-transfer-catalyzed asymmetric Michael reaction using newly-prepared chiral quaternary ammonium salts derived from l-tartrate", Tetrahedron Letters, vol. 43, No. 52, Dec. 23, 2002, pp. 9535-9537.
Llewellyn Lancaster N. et al., "Nucleophilicity in ionic liquids. 2. <1> Cation effects on halide nucleophilicity in a series of bis(trifluoromethylsulfonyl)imide ionic liquids", Journal of Organic Chemistry, vol. 67, No. 25, Dec. 13, 2002, pp. 8855-8861.
Shi, M. et al., "Synthesis and Reactions of (S)-N,N-Dialkyl-2-(hydroxydiarylmethyl)pyrrolidinium halides as chiral phase-transfer catalysts", Journal of Chemical Research, 1994, pp. 1460-1476.
Blicke, F. F.; Hotelling, E. B.J. Am. Chem. Soc. 1954, 76, 5099.
R.A. Aitkin, ARKIVOC 2002 (III) 63-70.
Ue, M., et al., S. J. Electrochem. Soc. 1994, 141, 2989-2996.
Braun, et al., Chem. Ber., 1924, 57, 187.
Braun, et al., Chem. Ber. 1916, 49, 970.
Thomas, et al., J. Am. Chem. Soc., 2003, EN 125, 29, 8870-88.
Braun, et al., Chem. Frank. 1937, 5, 979.
Uwe Monkowius et al., Chem. Munich, 2004, 259-263.

* cited by examiner

*Primary Examiner* — Brian McDowell
(74) *Attorney, Agent, or Firm* — Carrie Beatus

(57) ABSTRACT

A method for preparing a spiro quaternary ammonium system and electrolytes containing spiro quaternary ammonium cations, comprising a synthesizing step wherein a spiro ammonium system is formed in a medium that can serve as both the reaction solvent and as an electrolyte solvent. A one-solution method of making a non-aqueous electrolyte composition that comprises at least one of a spiro quaternary ammonium compound of the following formula:

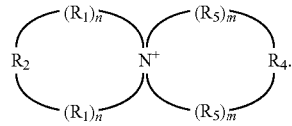

12 Claims, No Drawings

METHOD FOR SYNTHESIZING QUATERNARY AMMONIUM SYSTEMS

REFERENCE TO RELATED APPLICATIONS

This application is a divisional application of U.S. application Ser. No. 11/511,938 filed on Aug. 28, 2006, the contents of which are incorporated herein by reference.

BACKGROUND

1. Field of Invention

The invention relates generally to methods for synthesizing spiro quarternary ammonium systems. In particular, the invention relates to methods for preparing electrolytes comprising spiro quaternary ammonium salts.

2. Description of Related Art

Spiro quaternary ammonium systems have been found useful in a wide variety of applications. For example, spiro quaternary ammonium salts such as:

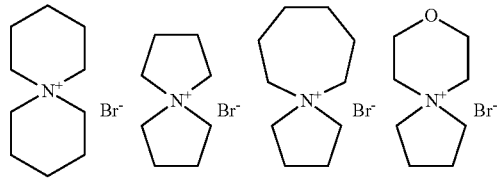

have been described by Blicke and Hotelling as novel cholinergic agents for the control of blood pressure (Blicke, F. F.; Hotelling, E. B. *J. Am. Chem. Soc.* 1954, 76, 5099) and characterized by 2D $^1$H—$^{13}$C NMR. (R. A. Aitkin, ARKIVOC 2002 (iii) 63-70).

More recently, and of particular interest to the present invention, spiro quaternary ammonium salts have been described in the preparation of non-aqueous electrolyte compositions, particular for use in energy storage devices such as electrochemical cells and capacitors with high capacity (i.e. ultra- or super-capacitors). (Ue, M., et al., *S. J. Electrochem. Soc.* 1994, 141, 2989-2996. See also U.S. Pat. No. 6,469,888 (Otsuki) and WO 2005/022571 (Ono).) Electrolytes containing spiro quaternary ammonium salts, especially spiro quaternary ammonium tetrafluoroborate and spiro quaternary ammonium bis(trifluoromethylsulfonyl)imide salts, are chemically and electrochemically stable, are compatible with carbon electrodes, have low viscosity and density, are highly conductive over a broad temperature range, and can provide high energy densities over a wide range of usable temperatures. These and other properties make electrolytes containing spiro quaternary ammonium tetrafluoroborate or bis(trifluoromethylsulfonyl)imide salts ideally suited for use in certain electrochemical storage devices, such as electrical double layer capacitors.

However, conventional methods for producing these salts for electrolyte applications are complicated and uneconomical. For example, one conventional method of producing a spiro quaternary ammonium tetrafluoroborate electrolyte involves a multi-step process wherein a spiro ammonium halide is first formed via alkylation of either ammonia (v. Braun, et al., *Chem. Ber.,* 1924, 57, 187) or cyclic amines, e.g. pyrrolidine, (v. Braun, et al., *Chem. Ber.* 1916, 49, 970) with dihalo-alkanes, preferably bromides or iodides. These halides can also be obtained via an organometallic reaction (Thomas, et al., *J. Am. Chem. Soc.,* 2003, EN 125, 29, 8870-88). The halide intermediate is further treated by membrane dialysis in water to form a spiro ammonium hydroxide solution, which can then be reacted with hydrofluoroboric acid to form the desired spiro quaternary ammonium tetrafluoroborate. To be useful in electrochemical devices, it is necessary to dry the spiro quaternary ammonium tetrafluoroborate composition to lower its water content. Finally, the spiro ammonium tetrafluoroborate is dissolved in a dried solvent or solvent mixture, and optionally passed through molecular drying sieves, to produce an anhydrous product. Depending on the concentration of water in the product and the desired purity, it may be necessary to employ more than one purification and/or drying step.

Applicants have recognized the need for a more cost effective means of producing electrolytes comprising spiro quaternary ammonium tetrafluoroborate salts. The present invention satisfies these and other needs.

SUMMARY OF THE INVENTION

The present invention provides an economical means for preparing spiro quaternary ammonium systems, and particularly electrolytes derived from such systems. Applicants have discovered a method wherein a single solvent or solvent mixture can function both as a reaction solvent for spiro quaternary ammonium synthesis, and as an electrolyte solvent for an electrolyte derived from such spiro quaternary ammonium systems. That is, Applicants have discovered a method wherein a spiro quaternary ammonium system is directly synthesized in a solvent that is also well suited for electrolyte applications, such solvents including, for example, acetonitrile (ACN), propylene carbonate (PC), gamma-butyrolactone (GBL), and the like. By synthesizing a spiro quaternary ammonium system directly in an electrolyte solvent, the present invention eliminates the need for separate reaction solvents and electrolyte solvents, thereby providing a simpler, more efficient, and more economical means of producing spiro quaternary ammonium electrolytes as compared to conventional methods.

Accordingly, a first object of the present invention is to provide an economical method for synthesizing spiro quaternary ammonium systems.

Another object of the present invention is to provide an economical method of producing spiro quaternary ammonium electrolytes.

Therefore, a first aspect of the present invention is a method of preparing a spiro quaternary ammonium system comprising a quaternization step wherein a spiro quaternary ammonium system is synthesized in a water miscible, organic electrolyte solvent. Certain preferred embodiments of the invention further comprise an additional step wherein a metal tetrafluoroborate or a metal bis(trifluoromethylsulfonyl)imid, is added to said solvent to form an electrolyte characterized by a spiro quaternary ammonium cation and a tetrafluoroborate or a bis(trifluoromethylsulfonyl)imide anion.

A second aspect of the present invention is a method of making a non-aqueous electrolyte comprising a quaternization step wherein a cyclic amine is quaternized, in an organic solvent and in the presence of a base, by an alkylation agent, such as dihalo-alkane or dihalo-heteroalkane, to form a solution comprising a spiro quaternary ammonium system; and optionally preparing a purified solution wherein at least a portion of any precipitate generated by the quaternization step is removed from the solution. Certain preferred embodiments further comprise a step of adding a metal tetrafluoroborate and/or metal bis(trifluoromethylsulfonyl)imide to the above-mentioned solution or purified solution to produce spiro quaternary ammonium tetrafluoroborate and/or bis(trifluoromethylsulfonyl)imide electrolytes.

DETAILED DESCRIPTION OF THE INVENTION

An economical method of synthesizing a spiro quaternary ammonium system is provided. Also provided is an economical method of producing a spiro quaternary ammonium electrolyte. More particularly, provided is a method wherein a cyclic amine is quaternized by an alkylating agent, in an organic solvent and in the presence of a base, to form a solution comprising a spiro quaternary ammonium system. Optionally, a purified solution of the solvent and spiro quaternary ammonium system can be obtained by removing from the solution at least a portion of any precipitate generated during the quaternization reaction. A metal tetrafluoroborate and/or a metal bis(trifluoromethylsulfonyl)imide may be added to this solution or purified solution to produce spiro quaternary ammonium tetrafluoroborate or bis(trifluoromethylsulfonyl)imide electrolytes.

Spiro systems, as used herein, are chemical substances (compounds, ions, etc.) having at least one spiro junction. A spiro junction exists when two ring structures are connected through a single center, such a quaternary nitrogen atom. The term "quaternary nitrogen" means a nitrogen atom bonded to four other atoms, such as, for example, four carbon atoms. The term "quaternary ammonium" generally means a univalent chemical ion comprising a quaternary nitrogen. Spiro quaternary ammonium systems of the present invention include those with monospiro and linear polyspiro (e.g. dispiro, trispiro, etc.) structures, for example:

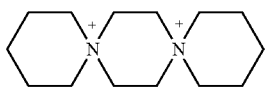

as well as spiro structures comprising at least one fused or bridged hydrocarbon and/or heterocyclic system, for example:

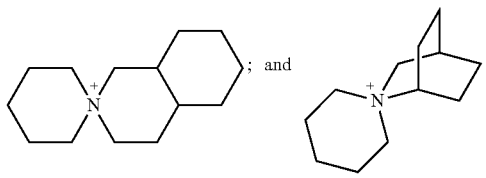

In addition, spiro quaternary ammonium salts according to the present invention include mono-, bis-, and tris- or higher quaternary structures such as, for example:

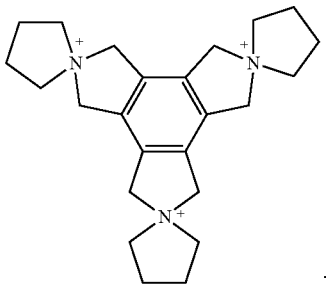

Although not wanting to be bound by any particular theory, Applicants believe that spiro quaternary ammonium tetrafluoroborate or bis(trifluoromethylsulfonyl)imide electrolytes are produced by reacting a cyclic amine, a polyhalogenated alkane or heteroalkane or a pseudohaloalkane, a metal base, and an alkali or alkaline-earth metal tetrafluoroborate or an alkaline bis(trifluoromethylsulfonyl)imide in a solvent. It is believed that the reaction proceeds according to the following general reaction scheme:

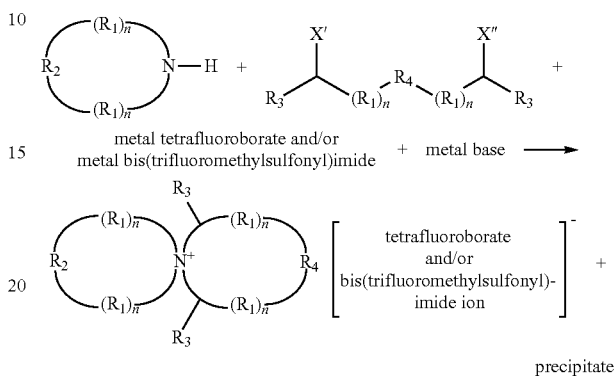

wherein
X' and X" are independently halogen or pseudohalogenides;
n is independent an integer from about 0 to about 6;
$R_1$ is independently $CH_2$, $CHF$, $CF_2$, $CH$, $CF$;
$R_2$ is $OF$, $CH_2$, $CR_3$, $CHF$, $CF_2$, $CHR_3$, $CR_3R_3$, $NH$, $O$, $S$, 3-8 member cyclic or heterocyclic, or a polycyclic or polyheterocyclic wherein each ring has 3 to 8 members;
$R_3$ is independently
(a) H;
(b) a $C_1$-$C_6$ alkyl, $C_1$-$C_6$ alkoxy, or $C_1$-$C_6$ alkenyl group; or
(c) heteroalkyl groups with a chain length of about 1 to about 6; and
$R_4$ is $OF$, $CH_2$, $CR_3$, $CHF$, $CF_2$, $CHR_3$, $CR_3R_3$, $NH$, $O$, or $S$.

Generally, any unsubstituted or substituted cyclic secondary or tertiary amine, optionally containing one or more additional heteroatom chosen from oxygen, sulfur, or nitrogen, is adaptable for use with the present invention. In certain preferred embodiments, secondary amines are used to synthesize spiro and poly-spiro compounds. However, in certain embodiments, tertiary amines may also be used to synthesize multi-spiro structures and/or spiro structures having a bridged portion. Tertiary amines are particularly useful when making poly-spiro structure from one or more other spiro-compounds or moieties.

Preferred cyclic secondary amines include, but are not limited to, those having one nitrogen atom, such as pyrrolidine, piperidine, and the like; those having a plurality of nitrogen atoms, such as imidazolidine, pyrazolidine, piperazine and the like; and those having heterocyclic structures such as those containing oxygen and/or sulfur atoms and/or additional nitrogen atoms, for example morpholine, imidazole, isothiazol, oxadiazol, 1,2,3-oxadiazol, 1,2,3-triazol, 1,3,4-thiadiazol and the like. These cyclic amines may be derived from any conventional method known in the art. Preferably, cyclic amines are introduced into the reaction as raw materials, but may also be produced from raw materials (e.g. ammonia, and the like) in situ.

Preferably, the cyclic amine will have from about 4 to about 7 ring members, and more preferably from about 5 to about 6 ring members. The present invention also contemplates methods in which a mixture of two or more cyclic amines of different structures or in which a plurality of dihalo-alkanes with different chain lengths or isomers or both are used for quaternization leading to a mixture of spiro salts.

Examples of cyclic amines for use with the present invention include, but are not limited to: pyrrolidine, piperidine, piperazine, morpholine, pyrrole, imidazole, pyrazole, pyrroline, pyrazine, pyrimidine, pyridazine, quinoline, β-carboline, phenoxazine, phenothiazine, oxazole, thiazole, furazan, indoline, imidazole, imidazolidine, quinuclidine, pyrazolidine, and the like. Preferred cyclic amines include secondary amines such as pyrrolidine, piperidine, imidazolidine, piperazine, morpholine, and the like; with pyrrolidine and piperidine being particularly preferred.

Generally, suitable alkylating agents for use with the present invention are those with two or more halogen atoms which are reactive enough to alkylate the nitrogen of the secondary amine. The potential ring size is an important element in the formation of a spiro compound because if the number of ring members is too small or too great, a bridged structure will form between two rings instead of a spiro structure. Thus, preferred alkylating agents have a branched, or more preferably straight, chain from about 3 to about 6 carbon atoms, and even more preferably about 4 to about 5 carbon atoms, between two halogen atoms. Even more preferred are straight chain alkylating agents with a halogen atom at each terminal end of the chain, such as dihalo-alkanes and dihalo-heteroalkanes.

Such compounds are halogenated with two halogen atoms independently selected from the group consisting of fluorine, chlorine, bromine, and iodine, with chlorine and bromine being preferred.

Preferred heteroalkanes are those which contain one or more atoms selected from the group consisting of oxygen and sulfur. Heteroalkanes containing one or more oxygen atoms in form of ether groups are known to be electrochemically stable and are therefore particularly preferred.

In certain embodiments, the alkylating agent has the formula:

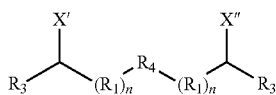

wherein X', X", n, $R_1$, $R_2$, $R_3$, and $R_4$ are defined as indicated above.

As a halogen, X' and/or X" can be independently fluorine, chlorine, bromine, iodine, with bromine or chlorine being preferred. For embodiments wherein X is fluorine, the reaction is preferably conducted in the presence of a catalyst. For this reason, embodiments wherein X is fluorine are not preferred. As a pseudohalogenides X' and/or X" can be independently, for example, tosyl (p-toluenesulfonyl), mesyl (methanesulfonyl), and/or triflyl (trifluoromethanesulfonyl)).

As a $C_1$-$C_6$ alkyl, $C_1$-$C_6$ alkoxy, or $C_1$-$C_6$ alkenyl group, $R_3$ can be unsubstituted or substituted, branched or non-branched, saturated or unsaturated. As a heteroalkyl, $R_3$ can be, for example, —$C_jH_{2j}OC_kH_{2k+1}$, —$C_jH_{2j}COC_kH_{2k+1}$ wherein j and k are positive integers and j+k is not greater than about 6.

Particularly preferred alkylating agents include

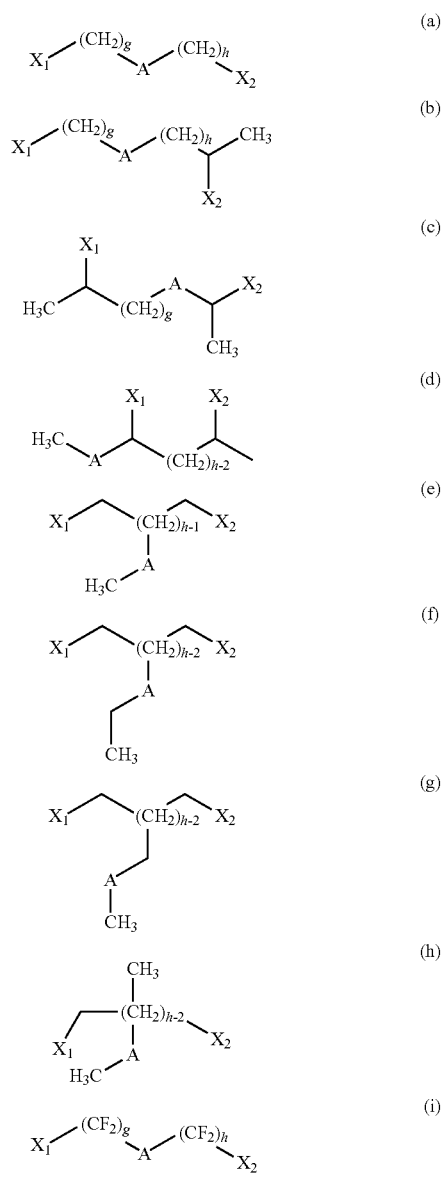

wherein
g and h are independently an integer from about 1 to about 4;
$X_1$ and $X_2$ are independently Cl, Br, or I; and
A=O, S, CHF, or $CF_2$.

Even more preferred are 1,3-dihalopropanes, 1,4-dihalobutanes, and 1,5-dihalopentanes wherein the two halogen atoms may be the same halogen or different halogens. Other highly preferred alkylating agents include perfluorodihaloalkanes having from about 3 to about 5 carbon atoms, such as for example, 1,4-dibromoperfluorobutane. Such perfluorodihaloalkanes are preferred in view of their high electrochemical stability.

The present invention also contemplates methods utilizing a mixture of two or more alkylating agents.

Preferably, the metal tetrafluoroborate are alkali metal or alkali-earth metal tetrafluoroborates, with potassium tetrafluoroborate being particularly preferred. The metal bis (trifluoromethylsulfonyl)imide compounds are preferably alkali-earth metal bis(trifluoromethylsulfonyl)imides. Although the reactants described in the above general reaction scheme include tetrafluoroborate and/or bis(trifluoromethylsulfonyl)imide compounds, it is understood that for the present invention, any moiety capable of forming an electrolyte anion can be used provided that the resulting electrolyte is electrochemically stable at a voltage of at least +/−1.5V.

Preferred bases are those comprising a metal ion. In certain preferred embodiments, the metal is chosen so that the precipitate formed has a solubility in the reaction media that allows at least a portion of it to be removed from the media via filtration, crystallisation, ion dialysis, reverse osmosis or some combination thereof. For example, a particular metal may be selected in such a way that its respective halide salt has a low solubility in the organic solvent chosen as the reaction media. Especially useful are combinations with high formation energies because they help to achieve high reaction yields therefore reducing or practically eliminating unreacted components left in solution.

Although the alkaline, earth alkaline or metal ions can be selected independently of each other, in some applications, purification will be easier if there is only a single ion type.

Bases which are generally suitable are inorganic compounds including alkali metal hydroxides and alkaline earth metal hydroxides, such as lithium hydroxide, sodium hydroxide, potassium hydroxide, calcium hydroxide, and the like; alkali metal and alkaline earth metal oxides such as lithium oxide, sodium oxide, calcium oxide, magnesium oxide, and the like; alkali metal hydrides and alkaline earth metal hydrides such as lithium hydride, sodium hydride, potassium hydride, calcium hydride, and the like; alkali metal amides such as lithium amide, sodium amide, potassium amide, and the like; alkali metal carbonates and alkaline earth metal carbonates such as lithium carbonate, calcium carbonate, and the like, and also alkali metal hydrogen carbonates such as sodium hydrogen carbonate and the like; basic metal oxidhydroxides such as or metal aluminium hydroxide, basic zinc oxide, basic tin oxide or basic zirconium oxide, titanium.oxidhydroxide, and the like; organometal compounds, in particular alkali metal alkyls such as methyllithium, butyllithium, phenyllithium, and the like; alkylmagnesium halides such as methylmagnesium chloride and the like; and also alkali metal alcoholates and alkaline earth metal alcoholates such as sodium methanolate, sodium ethanolate, potassium ethanolate, potassium tert-butanolate, dimethoxymagnesium, and the like.

Particularly preferred bases include alkali and alkaline-earth metal carbonates, phosphates, and hydroxides, according to one or more of the following formulas: $M_a(CO_3)_c$, $M_aH_b(CO_3)_c$, $M_a(PO_4)_c$, $M_aH_b(PO_4)_c$, and $M(OH)_c$, wherein M is an alkali or alkaline-earth metal and a, b, and c are integers in accordance with appropriate stoichiometry (e.g. if the base is potassium carbonate, then M=K, a=2 and c=3) or aluminium hydroxide. Even more preferred are alkali and alkaline-earth metal carbonates, with potassium carbonate being most preferred. The present invention also contemplates methods utilizing a mixture of two or more of the above-mentioned bases.

Preferred solvents for use with present invention are those that can be used both as a reaction medium and as an electrolyte solvent. A principle economic benefit of the present invention is the ability use a single solvent or mixture of solvents both as quaternization reaction medium and as an electrolyte solvent, thereby reducing the complexity and cost associated with conventional methods of making electrolytes having spiro quaternary ammonium salts. Especially useful solvents are those which have one or more of the following properties: organic-based and miscible with water, generally non-reactive, difficult to oxidize or reduce electrochemically, high dielectric constant, wide range of electric voltage stability, and operating temperature range of from about −60° C. to about 300° C.

Preferred organic solvents include mononitriles such as acetonitrile, propionitrile, phyenylacetonitrile, isobutylronitrile, benzonitrile, acrylonitrile, and the like; dinitriles such as succinonitrile, glutaronitrile, and the like; organic carbonates such as propylene carbonate, ethylene carbonate, diethyl carbonate, dimethyl carbonate, ethyl methyl carbonate and the like; lactones such as gamma-butyrolactone and related compounds; sulfolanes and methylsulfolane; ketones such as methylpropylketone, methylisobutylketone, and the like; N-methylpyrrolidone; N,N-dimethylformamide; dimethylacetamide; and mixtures of two or more of these.

In certain preferred embodiments, spiro quaternary ammonium systems comprise the following structure:

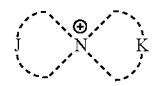

1. wherein J and K are independently alkyl, heteroalkyl, arylalkyl, heteroarylalkyl, or polycyclic moiety. The present invention also contemplates methods wherein polyspiro systems are formed having a plurality of the above-mentioned structures. For example, in certain embodiments the spiro quaternary ammonium systems comprise the structure:

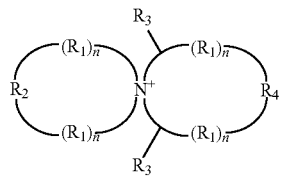

wherein
X', X", n, $R_1$, $R_2$, and $R_3$ are defined as indicated above, and $R_4$ is a quaternary ammonium spiro junction.

In addition, the present invention contemplates methods wherein a mixture of spiro and/or polyspiro systems having different structures are synthesized.

Preferred are spiro quaternary ammonium systems have from about 4 to about 7 members per ring, and even more preferably have at least one ring with from about 5 to about 6 members. According to certain highly preferred embodiments, spiro quaternary ammonium systems have the structure:

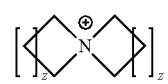

wherein z is independently an integer from about 0 to about 5, and more preferably from about 2 to about 3. Examples of such spiro quaternary ammonium systems include, but are not limited to, 6-azoniaspiro[5.5]undecane, 5-azoniaspiro[4.5]undecane, 5-azoniaspiro[4.4]nonane, and the like Preferred tetrafluoroborates include alkali tetrafluoroborates, such as lithium tetrafluoroborate, sodium tetrafluoroborate, and potassium tetrafluoroborate; alkaline earth tetrafluoroborates such as magnesium tetrafluoroborate, calcium tetrafluoroborate, strontium tetrafluoroborate, and barium tetrafluoroborate; and transition metal tetrafluoroborates, for example silver tetrafluoroborate or zinc fluoroborate; with potassium tetrafluoroborate and silver tetrafluoroborate being even more preferred.

Preferred bis(trifluoromethylsulfonyl)imides include alkali bis(trifluoromethylsulfonyl)imide, for example lithium bis(trifluoromethylsulfonyl)imide, sodium bis(trifluoromethylsulfonyl)imide, and potassium bis(trifluoromethylsulfonyl)imide, alkaline earth bis(trifluoromethylsulfonyl)imides, for example magnesium bis(trifluoromethylsulfonyl) imide, calcium bis(trifluoromethylsulfonyl)imide, strontium bis(trifluoromethylsulfonyl)imide, barium bis(trifluoromethylsulfonyl)imide or metal bis(trifluoromethylsulfonyl)imides with potassium bis(trifluoromethylsulfonyl)imide and sodium bis(trifluoromethylsulfonyl)imide being even more preferred.

Electrolyte having such spiro quaternary ammonium cations and tetrafluoroborate or bis(trifluoromethylsulfonyl)imide anions are known to possess properties that are especially beneficial for certain applications, e.g. in electrochemical cells were high ion conductivity together with high stability against electrochemical oxidation or reduction is required, for example supercapacitors. The spiro quaternary ammonium tetrafluoroborate or bis(trifluoromethylsulfonyl)imide salts might even be isolated and used in their melted for as ionic solvents for synthetic reactions.

In certain preferred embodiments, the quaternization reaction generates a precipitate by-product (e.g. insoluble portions of salts). Preferably, at least a portion of this precipitate is removed to produce an purified solution comprising at least a portion of the spiro quaternary ammonium system and at least a portion of the solvent. Any conventional means can be used to remove the precipitate, including filtration, ultrafiltration, dialysis, ion exchange, reverse osmosis, and the like. Preferably the precipitate is removed via a filtration process, more preferably cold filtration. In such processes, the purified product is the filtrate.

In certain preferred embodiments, a precipitate also forms with the addition of an alkali or alkaline-earth metal tetrafluoroborate or bis(trifluoromethylsulfonyl)imide to the solution or purified solution is likewise removed, e.g. via filtration. The resulting filtrate comprises the desired electrolyte in very high yields.

In certain preferred embodiments, the precipitate formed via the quaternization reaction and the precipitate formed via the metal tetrafluoroborate or bis(trifluoromethylsulfonyl) imide addition may be removed during a single step.

EXAMPLES

Example 1

Spiro-1,1'-bipyrrolidinium tetrafluoroborate, 5-azonia-spiro[4.4]nonane tetrafluoroborate Approximately 35.5 g (0.5 mol) of pyrrolidine, 72.5 g (0.5 mol) of 1,4-dichlorobutane, and 138 g (1.0 mol) of potassium carbonate are added to 500 ml of acetonitrile. The solution is mixed and heated to reflux for approximately 6 hours. The mixture is then cooled and then filtered.

A sample was taken and identified by $^1$H NMR (300 MHz; CDCl$_3$): 2.22 [m, CH2, 8H], 3.79 [m, CH2N, 8H]. The sample showed moderate selectivity.

Potassium tetrafluoroborate was added to the filtrate obtained above and was vigorously stirred. The precipitate was then removed via filtration.

The filtrate contains the desired product solution in very good yield.

Example 2

Spiro-1,1'-bipyrrolinium tetrafluoroborate, 5-azonia-spiro[4.4]nonane tetrafluoroborate Approximately 35.5 g (0.5 mol) of pyrrolidine, 72.5 g (0.5 mol) of 1,4-dichlorobutane, a catalytic amount of potassium bromide (and/or potassium iodide), and 138 g (1.0 mol) of potassium carbonate are added to 500 ml of acetonitrile. The solution is mixed and heated to reflux for approximately 6 hours. The mixture is then cooled and then filtered.

A sample was taken and identified by $^1$H NMR (300 MHz; CDCl$_3$): 2.22 [m, CH2, 8H], 3.79 [m, CH2N, 8H]. The sample showed moderate selectivity.

Potassium tetrafluoroborate was added to the filtrate obtained above and was vigorously stirred. The precipitate was then removed via filtration.

The filtrate contains the desired product solution in very good yield.

Example 3

Spiro-1,1'-bipyrrolinium tetrafluoroborate, 5-azonia-spiro[4.4]nonane tetrafluoroborate Approximately 35.5 g (0.5 mol) of pyrrolidine, 108 g (0.5 mol) of 1,4-dibromobutane, and 138 g (1.0 mol) of potassium carbonate are added to 500 ml of acetonitrile. The solution is mixed and heated to reflux for approximately 6 hours. The mixture is then cooled and then filtered.

A sample was taken and identified by $^1$H NMR (300 MHz; CDCl$_3$): 2.22 [m, CH2, 8H], 3.79 [m, CH2N, 8H]. The sample showed very good selectivity.

Potassium tetrafluoroborate was added to the filtrate obtained above and was vigorously stirred. The precipitate was then removed via filtration.

The filtrate contains the desired product solution in very good yield.

Example 4

Spiro-1,1'-bipyrrolinium tetrafluoroborate, 5-azonia-spiro[4.4]nonane tetrafluoroborate Approximately 35.5 g (0.5 mol) of pyrrolidine, 108 g (0.5 mol) of 1,4-dibromobutane, 138 g (1.0 mol) of potassium carbonate and 78.7 g (0.625 mol) potassium tetrafluoroborate are added to 500 ml of acetonitrile. The solution is mixed and heated to reflux for approximately 6 hours. The mixture is then cooled and then filtered.

A sample was taken and identified by $^1$H NMR (300 MHz; CDCl$_3$): 2.22 [m, CH2, 8H], 3.79 [m, CH2N, 8H]. The sample showed very good selectivity. The filtrate contains the desired product solution in excellent yield Example 5

Spiro-1,1'-bipyrrolinium bis(trifluoromethylsulfonyl)imide, 5-azonia-spiro[4.4]nonane bis(trifluoromethylsulfonyl)imide Approximately 35.5 g (0.5 mol) of pyrrolidine, 108 g (0.5 mol) of 1,4-dibromobutane, 138 g (1.0 mol) of potassium carbonate and 200 g (0.625 mol) potassium bis(trifluoromethylsulfonyl)imide are added to 500 ml of acetonitrile. The solution is mixed and heated to reflux for approximately 6 hours. The mixture is then cooled and then filtered.

A sample was taken and identified by $^1$H NMR (300 MHz; CDCl$_3$): 2.22 [m, CH2, 8H], 3.79 [m, CH2N, 8H]. The sample showed very good selectivity. The filtrate contains the desired product solution in excellent yield.

Example 6

Spiro(piperidin-1,1'-pyrrolidinium tetrafluoroborate; 5-azonia-spiro[4.5]decane; tetrafluoroborate Approximately 35.5 g (0.5 mol) of pyrrolidine, 115 g (0.5 mol) of 1,5-dibromopentane, and 138 g (1.0 mol) of potassium carbonate are added to 500 ml of acetonitrile. The solution is mixed and heated to reflux for approximately 6 hours. The mixture is then cooled and then filtered. Potassium tetrafluoroborate was added to the filtrate obtained above and was vigorously stirred. The precipitate was then removed via filtration. The filtrate contains the desired product solution in excellent yield.

Example 7

8-oxa-5-azonia-spiro[4.5]decane; tetrafluoroborate

Approximately 43.56 g (0.5 mol) of morpholine, 108 g (0.5 mol) of 1,4-dibromobutane, and 138 g (1.0 mol) of potassium carbonate are added to 500 ml of acetonitrile. The solution is mixed and heated to reflux for approximately 6 hours. The mixture is then cooled and then filtered. Potassium tetrafluoroborate was added to the filtrate obtained above and was vigorously stirred. The precipitate was then removed via filtration. The filtrate contains the desired product solution in moderate yield.

Example 8

8-oxa-5-azonia-spiro[4.5]decane; bis(trifluoromethylsulfonyl)imide

Approximately 43.56 g (0.5 mol) of morpholine, 108 g (0.5 mol) of 1,4-dibromobutane, and 138 g (1.0 mol) of potassium carbonate are added to 500 ml of propylen carbonate. The solution is mixed and heated to reflux for approximately 6 hours. The mixture is then cooled and then filtered. Potassium bis(trifluoromethylsulfonyl)imide was added to the filtrate obtained above and was vigorously stirred. The precipitate was then removed via filtration. The filtrate contains the desired product solution in moderate yield.

Example 9

4,4'-Spirobimorpholinium tetrafluoroborate; 3,9-dioxa-6-azonia-spiro[5.5]undecane; tetrafluoroborate Approximately 43.56 g (0.5 mol) of morpholine, 116 g (0.5 mol) of Bis-(2-bromoethyl)-ether and 138 g (1.0 mol) of potassium carbonate are added to 500 ml of acetonitrile. The solution is mixed and heated to reflux for approximately 6 hours. The mixture is then cooled and then filtered. Potassium tetrafluoroborate was added to the filtrate obtained above and was vigorously stirred. The precipitate was then removed via filtration. The filtrate contains the desired product solution in moderate yield.

Example 10

Spiro-1,1'-bipyrrolidinium tetrafluoroborate, 5-azonia-spiro[4.4]nonane tetrafluoroborate Approximately 35.5 g (0.5 mol) of pyrrolidine, 199 g (0.5 mol) of 1,4-ditosylbutane, and 138 g (1.0 mol) of potassium carbonate are added to 500 ml of acetonitrile. The solution is mixed and heated to reflux for approximately 6 hours. The mixture is then cooled and then filtered.

A sample was taken and identified by $^1$H NMR (300 MHz; CDCl$_3$): 2.22 [m, CH2, 8H], 3.79 [m, CH2N, 8H]. The sample showed moderate selectivity.

Potassium tetrafluoroborate was added to the filtrate obtained above and was vigorously stirred. The precipitate was then removed via filtration.

The filtrate contains the desired product solution in moderate yield.

Examples 11-31

The prophetic examples in Table 1 have been carried out as described in Example 1, except using different alkylating agents.

TABLE 1

| Example No. | Reactants | Spiro Complex Formed | | Results |
|---|---|---|---|---|
| 1. | 0.5 mol of pyrrolidine<br>0.5 mol 1,4-dichlorobutane | 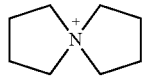 | BF$_4^-$ | solution in acetonitrile in good yield |
| 11. | 0.5 mol of pyrrolidine<br>0.4 mol 1,4-dichlorobutane<br>0.1 mol 1,4-dibromobutane |  | BF$_4^-$ | solution in acetonitrile in good overall yield |
| 12. | 0.5 mol of pyrrolidine<br>0.25 mol 1,4-dichlorobutane<br>0.25 mol 1,4-dibromobutane | 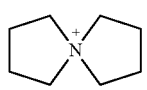 | BF$_4^-$ | solution in acetonitrile in good overall yield |

TABLE 1-continued

| Example No. | Reactants | Spiro Complex Formed | Results |
|---|---|---|---|
| 13. | 0.5 mol of pyrrolidine<br>0.1 mol 1,4-dichlorobutane<br>0.4 mol 1,4-dibromobutane | spiro pyrrolidinium BF$_4^-$ | solution in acetonitrile in excellent overall yield |
| 14. | 0.5 mol of pyrrolidine<br>0.5 mol 1,4-dibromobutane | spiro pyrrolidinium BF$_4^-$ | solution in acetonitrile in good yield |
| 15. | 0.5 mol of pyrrolidine<br>0.5 mol 1-chloro-4-bromobutane | spiro pyrrolidinium BF$_4^-$ | solution in acetonitrile in excellent overall yield |
| 16. | 0.5 mol of pyrrolidine<br>0.25 mol 1-chloro-4-bromobutane<br>0.25 mol 1,4-dibromobutane | spiro pyrrolidinium BF$_4^-$ | solution in acetonitrile in excellent overall yield |
| 17. | 0.5 mol of pyrrolidine<br>0.1 mol 1-chloro-4-bromobutane<br>0.4 mol 1,4-dibromobutane | spiro pyrrolidinium BF$_4^-$ | solution in acetonitrile in excellent overall yield |
| 18. | 0.5 mol of pyrrolidine<br>0.25 mol 1-chloro-4-bromobutane<br>0.25 mol 1,4-dichlorobutane | spiro pyrrolidinium BF$_4^-$ | solution in acetonitrile in excellent overall yield |
| 19. | 0.5 mol of pyrrolidine<br>0.1 mol 1-chloro-4-bromobutane<br>0.4 mol 1,4-dichlorobutane | spiro pyrrolidinium BF$_4^-$ | solution in acetonitrile in excellent overall yield |
| 20. | 0.5 mol of pyrrolidine<br>0.5 mol 1,4-dijodobutane | spiro pyrrolidinium BF$_4^-$ | solution in acetonitrile in moderate yield |
| 21. | 0.5 mol of pyrrolidine<br>0.5 mol 1,4-difluorobutane | spiro pyrrolidinium BF$_4^-$ | solution in acetonitrile in very low yield |
| 22. | 0.5 mol of pyrrolidine<br>0.5 mol 1,4-Dibromoperfluorobutane | perfluorinated spiro pyrrolidinium BF$_4^-$ | solution in acetonitrile in excellent overall yield |
| 23. | 0.5 mol of pyrrolidine<br>0.5 mol 1,5-dibromopentane | spiro piperidinium BF$_4^-$ | solution in acetonitrile in good yield |
| 24. | 0.5 mol of pyrrolidine<br>0.5 mol 1,5-dibromopentane | methyl-substituted spiro BF$_4$ | solution in acetonitrile good yield |
| 25. | 0.5 mol of pyrrolidine<br>0.5 mol 2,5-dibromohexane | dimethyl-substituted spiro BF$_4^-$ | solution in acetonitrile in moderate yield |
| 26. | 0.5 mol of pyrrolidine<br>0.5 mol bis(2-bromoethyl) ether | morpholinium-spiro BF$_4^-$ | solution in acetonitrile in good overall yield |

TABLE 1-continued

| Example No. | Reactants | Spiro Complex Formed | Results |
|---|---|---|---|
| 27. | 0.5 mol of pyrrolidine<br>0.5 mol 2-bromoethyl 2-chloroethyl ether | 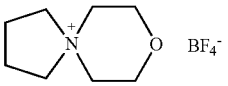 | solution in acetonitrile in good overall yield |
| 28. | 0.5 mol of pyrrolidine<br>0.5 mol bis(2-chloroethyl) ether | 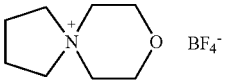 | solution in acetonitrile in moderate yield |
| 29. | 0.5 mol of pyrrolidine<br>0.5 mol 1-bromomethyl 2-chloroethyl ether | 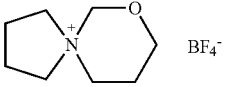 | solution in acetonitrile in excellent yield |
| 30. | 0.5 mol of pyrrolidine<br>0.5 mol 2-bromoethyl 1-chloromethyl ether | 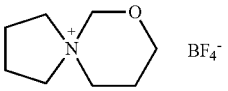 | solution in acetonitrile in good yield |
| 31. | 0.5 mol of pyrrolidine<br>0.5 mol bis-(2-chloro-1-methylethyl)-ether | 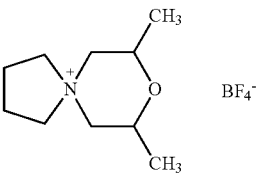 | solution in acetonitrile in good yield |

Examples 32-43

The prophetic examples in Table 2 have been carried out as described in Example 4 using different cyclic amines and alkylating agents.

TABLE 2

| Example No. | Reactants | Spiro Complex Formed | Results |
|---|---|---|---|
| 4. | 0.5 mol of pyrrolidine<br>0.5 mol 1,4-dibromobutane | 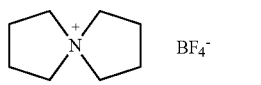 | solution in acetonitrile in excellent overall yield |
| 32. | 0.5 mol piperidine<br>0.5 mol 1,5-dibromopentane | 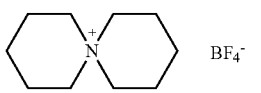 | solution in acetonitrile in good yield |
| 33. | 0.5 mol piperidine<br>0.5 mol 1,4-dibromobutane | 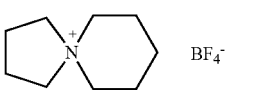 | solution in acetonitrile in excellent yield |
| 34. | 0.5 mol of morpholine<br>0.5 mol 1,4-dibromobutane | 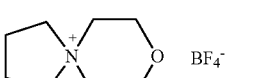 | solution in acetonitrile in moderate yield |
| 35. | 0.5 mol of morpholine<br>0.5 mol Bis(2-chloroethyl)ether | 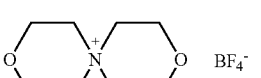 | solution in acetonitrile in low yield |
| 36. | 0.5 mol of morpholine<br>0.5 mol Bis(2-chloroethyl)ether | 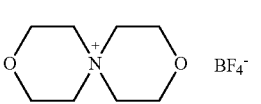 | solution in acetonitrile in moderate yield |

TABLE 2-continued

| Example No. | Reactants | Spiro Complex Formed | Results |
|---|---|---|---|
| 37. | 0.5 mol of morpholine 0.5 mol 2-bromoethyl 1-bromomethyl ether | 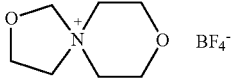 BF$_4^-$ | solution in acetonitrile in moderate yield |
| 38. | 0.25 mol of piperazine, 0.5 mol 1,4-dibromobutane | 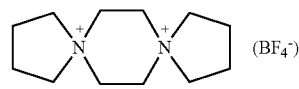 (BF$_4^-$)$_2$ | solution in acetonitrile in moderate yield |
| 39. | 0.25 mol of piperazine, 0.5 mol 1,5-dibromopentane | 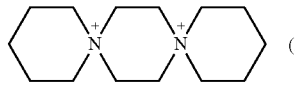 (BF$_4^-$)$_2$ | solution in acetonitrile in moderate yield |
| 40. | 0.25 mol imidazolidine 0.5 mol 1,4-dibromobutane | 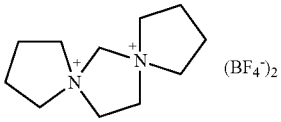 (BF$_4^-$)$_2$ | solution in acetonitrile in moderate yield |
| 41. | 0.25 mol pyrazolidine 0.5 mol 1,4-dibromobutane | 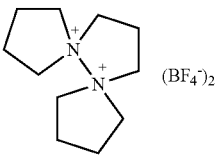 (BF$_4^-$)$_2$ | solution in acetonitrile in in low yield |
| 42. | 0.75 mol imidazolidine 0.5 mol 1,4-dibromobutane | 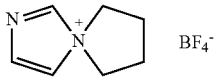 BF$_4^-$ | solution in acetonitrile in low yield |
| 43. | 0.5 mol of oxadiazole 0.5 mol 1,4-dibromobutane | 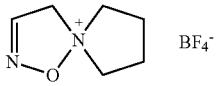 BF$_4^-$ | solution in acetonitrile in low yield |

Examples 44-63

The prophetic examples in Table 3 have been carried out as described in example 4 using different bases, metal salts and solvent

TABLE 3

| Example No. | Reactants | Spiro Complex Formed | Results |
|---|---|---|---|
| 4. | 1.0 mol potassium carbonate, 0.625 mol potassium tetrafluoroborate, 500 ml acetonitrile | 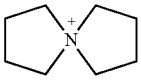 BF$_4^-$ | solution in acetonitrile in excellent overall yield |
| 44. | 1.0 mol potassium carbonate, 0.625 potassium tetrafluoroborate, 500 ml acetonitrile | 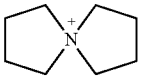 BF$_4^-$ | solution in acetonitrile in excellent overall yield |
| 45. | 1.0 mol potassium carbonate, 200 g (0.625 mol) potassium bis(trifluoromethylsulfonyl)imide, 500 ml acetonitrile |  (CF$_3$SO$_2$)$_2$N$^-$ | solution in acetonitrile in excellent overall yield |
| 46. | 1.0 mol potassium carbonate, 0.625 mol potassium tetrafluoroborate, 500 ml propylene carbonate | 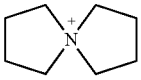 BF$_4^-$ | solution in propylene carbonate in excellent overall yield |

TABLE 3-continued

| Example No. | Reactants | Spiro Complex Formed | Results |
|---|---|---|---|
| 47. | 1.0 mol potassium carbonate, 0.625 mol potassium tetrafluoroborate, 500 ml gamma-butyrolactone | spiro ammonium $BF_4^-$ | solution in gamma-butyrolactone in excellent overall yield |
| 48. | 1.0 mol potassium carbonate, 200 g (0.625 mol) potassium bis(trifluoromethylsulfonyl)imide, 500 ml gamma-butyrolactone | spiro ammonium $(CF_3SO_2)_2N^-$ | solution in gamma-butyrolactone in excellent overall yield |
| 49. | 1.0 mol potassium carbonate, 0.625 mol potassium tetrafluoroborate, 250 ml propylene carbonate, 250 ml ethylene carbonate | spiro ammonium $BF_4^-$ | solution in propylene carbonate ethylene carbonate (1:1) in excellent overall yield |
| 50. | 1.0 mol potasssium carbonate, 200 g (0.625 mol) potassium bis(trifluoromethylsulfonyl)imide, 250 ml propylene carbonate, 250 ml ethylene carbonate | spiro ammonium $(CF_3SO_2)_2N^-$ | solution in propylene carbonate ethylene carbonate (1:1) in excellent overall yield |
| 51. | 1.0 mol potassium carbonate, 0.625 mol potassium tetrafluoroborate, 250 ml acetonitrile, 160 ml propylene carbonate, 90 ml ethylene carbonate | spiro ammonium $BF_4^-$ | solution in a belnd of acetonitrile, propylene carbonate and ethylene carbonate in excellent overall yield |
| 52. | 1.0 mol potassium carbonate, 0.625 mol potassium tetrafluoroborate 250 ml acetonitrile, 200 ml ethylene carbonate, 100 ml gamma-butyrolactone | spiro ammonium $BF_4^-$ | solution in a blend of acetonitrile, ethylene carbonate and gamma-butyrolactone in excellent overall yield |
| 53. | 1.0 mol potassium carbonate, 200 g (0.625 mol) potassium bis(trifluoromethylsulfonyl)imide, 250 ml acetonitrile, 200 ml ethylene carbonate, 100 ml gamma-butyrolactone | spiro ammonium $(CF_3SO_2)_2N^-$ | solution in a blend of acetonitrile, ethylene carbonate and gamma-butyrolactone in excellent overall yield |
| 54. | 1.0 mol potassium carbonate, 0.625 mol potassium tetrafluoroborate, 500 ml sulfolane | spiro ammonium $BF_4^-$ | solution in sulfolane in low overall yield |
| 55. | 1.0 mol potassium carbonate, 200 g (0.625 mol) potassium bis(trifluoromethylsulfonyl)imide, 500 ml sulfolane | spiro ammonium $(CF_3SO_2)_2N^-$ | solution in sulfolane in low overall yield |
| 56. | 1.0 mol potassium carbonate, 0.625 mol potassium tetrafluoroborate, 250 ml sulfolane, 250 ml ethylene carbonate | spiro ammonium $BF_4^-$ | solution in in a blend of ethylene carbonate and sulfolane in good overall yield |

TABLE 3-continued

| Example No. | Reactants | Spiro Complex Formed | | Results |
|---|---|---|---|---|
| 57. | 1.0 mol potassium carbonate, 200 g (0.625 mol) potassium bis(trifluoromethylsulfonyl)imide, 250 ml sulfolane, 250 ml ethylene carbonate | 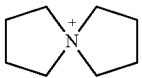 | (CF$_3$SO$_2$)$_2$N$^-$ | solution in a blend of ethylene carbonate and sulfolane in good overall yield |
| 58. | 1.0 mol sodium carbonate, 0.625 mol potassium tetrafluoroborate, 500 ml acetonitrile | 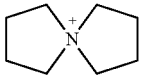 | BF$_4^-$ | solution in acetonitrile in excellent overall yield |
| 59. | 1.0 mol sodium carbonate, 0.625 potassium tetrafluoroborate, 500 ml acetonitrile | 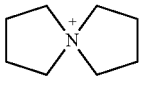 | BF$_4^-$ | solution in acetonitrile in excellent overall yield |
| 60. | 1.0 mol sodium carbonate, 0.625 mol potassium tetrafluoroborate, 500 ml acetonitrile | 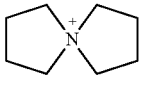 | BF$_4^-$ | solution in acetonitrile in excellent overall yield |
| 61. | 1.0 mol potassium carbonate, 0.625 mol zinc tetrafluoroborate, 500 ml acetonitrile | 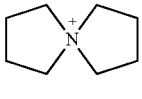 | BF$_4^-$ | solution in acetonitrile in excellent overall yield |
| 62. | 0.9 mol potassium carbonate, 0.1 mol aluminum hydroxide, 0.625 mol potassium tetrafluoroborate, 500 ml acetonitrile | 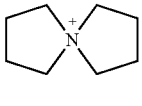 | BF$_4^-$ | solution in acetonitrile in excellent overall yield |
| 63. | 1.0 mol sodium carbonate, 0.625 mol silver tetrafluoroborate, 500 ml acetonitrile | 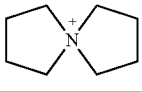 | BF$_4^-$ | solution in acetonitrile in excellent overall yield |

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A one-solution method of making a non-aqueous electrolyte composition that comprises at least one of a spiro quaternary ammonium tetrafluoroborate compound or a spiro quaternary ammonium bis(trifluoromethylsulfonyl)imide compound and an electrolyte solvent, the method comprising:
reacting in the electrolyte solvent a cyclic amine, an alkylating agent, and at least one of a metal tetrafluoroborate or a metal bis(trifluoromethylsulfonyl)imide in the presence of a base, thereby forming the electrolyte composition,
wherein said electrolyte solvent is selected from the group consisting of acetonitrile, succinonitrile, glutaronitrile, propionitrile, phenylacetonitrile, isobutylronitrile, benzonitrile, acrylonitrile, propylene carbonate, ethylene carbonate, diethyl carbonate, dimethyl carbonate, ethyl methyl carbonate, methyl 2,2,2-trifluoroethyl carbonate, gamma-butyrolactone, methylpropylketone, methylisobutylketone, N-methylpyrrolidone, N,N-dimethylformamide, dimethylacetamide, sulfolane, and mixtures of two or more thereof, and
wherein said cyclic amine comprises a cyclic secondary amine moiety having the formula:

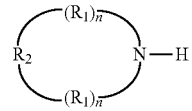

wherein

R$_1$ is CHF or CF$_2$;

n is an integer from 1 to 6;

R$_2$ is CHF, CF$_2$, CHR$_3$, CR$_3$R$_3$, NH, O, or S; and

R$_3$ is independently (a) H;

(b) a C$_1$-C$_6$ alkyl, C$_1$-C$_6$ alkoxy, or C$_2$-C$_6$ alkenyl group; or (c) a heteroalkyl group with a chain length of 1 to about 6 atoms;

wherein said at least one of a spiro quaternary ammonium tetrafluoroborate compound or a spiro quaternary ammonium bis(trifluoromethylsulfonyl)imide compound comprises the structure:

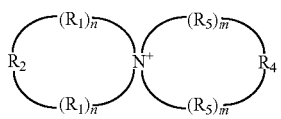

wherein n is an integer from 1 to 6;

m is an integer from 1 to 6;

$R_1$, $R_2$ and $R_3$ are as defined above;

$R_4$ is $CFR_3$, $CH_2$, CHF, $CF_2$, $CHR_3$, $CR_3R_3$, NH, O or S; and $R_5$ is independently $CH_2$, CHF, $CF_2$, $CFR_3$, $CHR_3$, or $CR_3R_3$.

2. The method of claim 1 further comprising purifying the composition by removing at least a portion of a precipitate formed.

3. The method of claim 1 wherein said at least one of a spiro quaternary ammonium tetrafluoroborate compound or a spiro quaternary ammonium bis(trifluoromethylsulfonyl)imide compound comprises at least one of 6-azoniaspiro[5.5]undecane, 5-azoniaspiro[4.5]undecane, or 5-azoniaspiro[4.4]nonane.

4. The method of claim 1 wherein said metal tetrafluoroborate is potassium tetrafluoroborate and said metal bis(trifluoromethylsulfonyl)imide is potassium bis(trifluoromethylsulfonyl)imide.

5. The method of claim 1 wherein said alkylating agent is selected from the group consisting of 1,4-dichlorobutane, 1,5-dichloropentane, 1,4-dibromobutane, 1,5-dibromopentane, 1,5-chlorobromopentane, 1,4-dichloropentane, 1,4-dibromopentane, 1-Bromo-4-chlorobutane, bis(2-bromoethyl) ether, 2-bromoethyl 2-chloroethyl ether, bis(2-chloroethyl) ether; 1-bromomethyl 2-chloroethyl ether, 2-bromoethyl 1-chloromethyl ether, 1,4-ditosylbutane, 1,5-ditosylpentane, 1,5-tosylbromopentane, 1,4-ditosylpentane, 1-bromo-4-tosylbutane, 1,4-dimesylbutane, 1,5-dimesylpentane, 1,4-bromomesylbutane, 1,5-mesylbromopentane, 1,4-dimesylpentane, 1-bromo-4-mesylbutane, 1,4-ditriflylbutane, 1,5-ditriflylpentane, 1,5-triflylbromopentane, 1,4-ditriflylpentane, and 1-bromo-4-triflylbutane.

6. The method of claim 1 wherein said base is selected from the group consisting of alkali metal hydroxides, alkaline earth metal hydroxides, alkali metal oxides, alkaline earth metal oxides, alkali metal hydrides, alkaline earth metal hydrides, alkali metal amides, alkali metal carbonates, alkaline earth metal carbonates, alkali metal hydrogen carbonates, basic metal oxidhydroxides, organometallic compounds, alkylmagnesium halides, alkali metal alcoholates and alkaline earth metal alcoholates.

7. The method of claim 1 wherein said base has a formula selected from the group consisting of $M_a(CO_3)_c$, $M_aH_b(CO_3)_c$, $M_a(PO_4)_c$, $M_aH_b(PO_4)_c$, and $M(OH)_c$, wherein M is an alkali or alkaline-earth metal, a is an integer from about 1 to about 2, b and c are independently an integer from 0 to about 2.

8. The method of claim 1 wherein $R_3$ is H; and $R_4$ is $CH_2$.

9. The method of claim 1 wherein said electrolyte composition comprises a spiro quaternary ammonium compound selected from the group consisting of 6-azoniaspiro[5.5]undecane tetrafluoroborate, 5-azoniaspiro[4.5]decane tetrafluoroborate, 5-azoniaspiro[4.4]nonane tetrafluoroborate, 6-azoniaspiro[5,5]undecane bis(trifluoromethylsulfonyl)imide, 5-azoniaspiro[4.5]decane bis(trifluoromethylsulfonyl)imide, and 5-azoniaspiro[4.4]nonane bis(trifluoromethylsulfonyl)imide.

10. The method of claim 1, wherein said electrolyte solvent is selected from the group consisting of succinonitrile, glutaronitrile, propionitrile, phenylacetonitrile, isobutyronitrile, benzonitrile, acrylonitrile, propylene carbonate, ethylene carbonate, diethyl carbonate, dimethyl carbonate, ethyl methyl carbonate, methyl 2,2,2-trifluoroethyl carbonate, gamma-butryolactone, methylpropylketone, methylisobutylketone, N-methylpyrrolidone, N,N-dimethylformamide, dimethylacetamide, sulfolane, and mixtures of two or more thereof.

11. The method of claim 1, wherein said electrolyte solvent is selected from the group consisting of propylene carbonate, ethylene carbonate, diethyl carbonate, dimethyl carbonate, ethyl methyl carbonate, methyl 2,2,2-trifluoroethyl carbonate, and mixtures of two or more thereof.

12. The method of claim 1 further comprising purifying the composition by removing through filtration at least a portion of a precipitate formed, wherein the filtrate comprises the at least one of a spiro quaternary ammonium tetrafluoroborate compound or a spiro quaternary ammonium bis(trifluoromethylsulfonyl)imide compound in the electrolyte solvent.

* * * * *